(12) United States Patent
Nerenberg et al.

(10) Patent No.: US 7,135,283 B1
(45) Date of Patent: Nov. 14, 2006

(54) TOPOISOMERASE TYPE II GENE POLYMORPHISMS AND THEIR USE IN IDENTIFYING DRUG RESISTANCE AND PATHOGENIC STRAINS OF MICROORGANISMS

(75) Inventors: Michael Nerenberg, La Jolla, CA (US); Ray Radtkey, San Diego, CA (US); Prashant Mehta, San Diego, CA (US); Dana Vollmer, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/193,291

(22) Filed: Nov. 17, 1998

(51) Int. Cl.
*C12Q 1/68* (2006.01)
*C12P 19/34* (2006.01)
*C07H 21/04* (2006.01)
*C12N 9/90* (2006.01)

(52) U.S. Cl. .................. 435/6; 435/91.2; 435/233; 536/23.2; 536/23.7; 536/24.32; 536/24.33

(58) Field of Classification Search ............ 435/6, 435/91.2, 91.5, 91.51; 536/23.1, 23.2, 23.7, 536/24.32, 24.33, 23.32, 23.33
See application file for complete search history.

(56) References Cited

U.S. PATENT DOCUMENTS

| | | |
|---|---|---|
| 4,787,963 A | 11/1988 | MacConnell |
| 5,445,934 A | 8/1995 | Fodor et al. |
| 5,527,670 A | 6/1996 | Stanley |
| 5,605,662 A | 2/1997 | Heller et al. |
| 5,632,957 A | 5/1997 | Heller et al. |
| 5,645,994 A | 7/1997 | Huang ............... 435/435 |
| 5,648,482 A * | 7/1997 | Meyer ............... 536/24.33 |
| 5,653,939 A | 8/1997 | Hollis et al. |
| 5,849,486 A | 12/1998 | Heller et al. |
| 6,015,666 A * | 1/2000 | Springer et al. ........ 435/6 |
| 6,017,696 A | 1/2000 | Heller |
| 6,048,690 A | 4/2000 | Heller et al. |
| 6,051,380 A | 4/2000 | Sosnowski et al. |
| 6,054,270 A | 4/2000 | Southern |

OTHER PUBLICATIONS

James P. Nataro & James B. Kaper; "Diarrheagenic *Escherichia coli*"; (Jan. 1998) vol. 11 No. 1, pp. 142-209; *Clinical Microbiology Reviews*.

K. L. MacDonald & M.T. Osterholm; "The Emergency of *Escherichia coli* 0157:H7 Infection in the United States: The Changing Epidemiology of Foodborne Disease"; (May 5, 1993) vol. 269 No. 17; pp. 2264-2267; *The Journal of the American Medical Association*.

Jesse Majkowski; "Strategies for Rapid Response to Emerging Foodborne Microbial Hazards"; (Oct.-Dec. 1997) vol. 3 No. 4; pp. 551-554; *Emerging Infectious Diseases*.

Bala Swaminathan & Peter Feng; "Rapid Detection of Food-Borne Pathogenic Bacteria"; (1994) vol. 48; pp. 401-426; *Annual Review of Microbiology*.

(Continued)

*Primary Examiner*—Diana B. Johannsen
(74) *Attorney, Agent, or Firm*—O'Melveny & Myers LLP

(57) ABSTRACT

Novel polymorphisms of prokaryotic topoisomerase type II Gyr A, Gyr B and parC gene loci are provided. These polymorphisms differentiate very closely related organisms and provide a means to identify pathogenicity and drug resistance. For example, drug resistance such as resistance to methicillin, a drug which is not metabolically tied to topoisomerase function, may be determined by polymorphisms in the Gyrase A locus. Identification of such drug resistance by such unrelated loci is indicative of heretofore unrecognized [sub]species of *Staphylococcus aureus*.

3 Claims, 8 Drawing Sheets

GYRASE A: ALLELE-SPECIFIC AMPLIFICATION

OTHER PUBLICATIONS

Robert D. Arbeit; "Laboratory Procedures for the Epidemiologic Analysis of Microorganisms"; pp. 190-208; *Manual of Clinical Microbilogy*.

A. Christian Whelen & David H. Persing; "The Role of Nucleic Acid Amplification and Detection in the Clinical Microbiology Laboratory"; (1996) vol. 50; pp. 349-373; *Annual Review of Microbiology*.

William G. Weisburg, Susan M. Barns, Dale A. Pelletier & David J. Lane; "16S Robosomal DNA Amplification for Phylogenetic Study"; (Jan. 1991) vol. 173 No. 2; pp. 697-703; *Journal of Bacteriology*.

Jean-Marc Neefs, Yves Van de Peer, Peter De Rijk, Sabine Chapelle & Ruprt De Wachter; "Compilation of Small Ribosomal Subunit RNA Structures"; (Jul. 1, 1993) vol. 21 No. 13; pp. 3025-3049; *Nucleic Acids Research*.

Wai Mun Huang; "Bacterial Diversity Based On Type II DNA Topoisomerase Genes"; (1996) vol. 30 pp. 79-107; *Annual Review of Genetics*.

Isabelle Guillemin, Emmanuelle Cambau & Vincent Jarlier; "Sequences of Conserved Region in the A Subunit of DNA Gyrase from Nine Species of the Genus Mycobacterium: Phylogenetic Analysis and Implication for Intrinsic Susceptibility to Quinolones"; (Sep. 1995) vol. 39 No. 9; pp. 2145-2149; *Antimicrobial Agents & Chemotherapy*.

Gary J. Olsen, Carl R. Woese & Ross Overbeek; "Minireview"; (Jan. 1994) vol. 176 No. 1; pp. 1-6; *Journal of Bacteriology*.

Loreen A. Herwaldt & Richard P. Wenzel; "Dynamics of Hospital-Acquired Infection"; Sixth Edition; pp. 159-181; *Manual of Clinical Microbiology*.

Margaret M. Morita, BA, CIC; "Methicillin-Resistant *Staphylococcus aureus* Past, Present & Future"; (Sep. 1993) vol. 28 No. 3; pp. 625-637; *The Nursing Clinics of North America*.

Gordon L. Archer & Debra M. Niemeyer; "Origin and Evolution of DNA Associated With Resistance to Methicillin in Staphylococci"; (1994) vol. 2; *Trends in Microbiology Virulence, Infection and Pathogenesis*.

Kazuhisa Murakami, Wakio Minamide, Koji Wada, Etuo Nakamura, Hiroshi Teraoka & Sachihiko Watanabe; Identification of Methicillin-Resistant Strains of Staphylococci by Polymerase Chain Reaction; (Oct. 1991) vol. 29 No. 10; pp. 2240-2244; *Journal of Clinical Microbiology*.

Shangwei Wu, Claudia Piscitelli, Herminia de Lencastre & Alexander Tomasz; "Tracking the Evolutionary Origin of the Methicillin Resistance Gene: Cloning and Sequencing of a Homologue of mecA from a Methicillin Susceptible Strain of *Staphylococcus sciuri*"; (1996) vol. 2 No. 4; pp. 435-441; *Microbial Drug Resistance*.

Matthias, Husmann, Alix Feddersen, Annette Steitz, Claudia Freytag & Sucharit Bhardi; "Simultaneous Identification of Campylabacters and Prediction of Quinolone Resistance by Comparative Sequence Analysis"; (Sep. 1997) vol. 35 No. 9; pp. 2398-2400; *Journal of Clinical Microbiology*.

Tong Wang, Mayumi Tanaka & Kenichi Sato; "Detection of grlA and gyrA Mutations in 344 *Staphylococcus aureus* Strains"; (Feb. 1998) vol. 42 No. 2; pp. 236-240; *Antimicrobial Agents & Chemotherapy*.

\* cited by examiner

Gyrase A  876 amino acids

ParC  753 amino acids

Gyrase A  888 amino acids

```
                    10         20         30         40         50         60         70         80         90
                    |          |          |          |          |          |          |          |          |
SEQ ID NO: 27       CGTTGGTGACGTAATCGGTAAATACCATCCCCATGGTGACTCGGCGGTCTATGACACGATCGTCCGCATGGCGCAGCCATTCTCGCTGCGT
SEQ ID NO: 1   ESCO strain 0157  . . . . . . . . . . . . . . . . . . . . . . . . . . . . . . . . . . . . . . A . T . . . . . . . . T . . . . . . . . . . . . . . . . .
SEQ ID NO: 1   ESCO strain 055   . . . . . . . . . . . . . . . . . . . . . . . . . . . . . . . . . . . . . . A . T . . . . . . . . T . . . . . . . . . . . . . . . . .
```

Fig. 6

```
                    10         20         30         40         50         60         70         80         90
                    |          |          |          |          |          |          |          |          |
SEQ ID NO: 28       ACCGAATCCCGGTTGTCGAAATATTCCGAGCTGCTATTGAGCGAGCTGCTATTGAGCGAGGGACGGCTGACTGGGTGCCAAACTTCGACGGCACTT
SEQ ID NO: 2   ESCO strain 0157  . . . . . . . . . . . . . . . . . . . . . . . . . . . . . . . . . . . . . . . . T . . . . . . . . . . . . . . . . . . . . . . . . . . . .
SEQ ID NO: 2   ESCO strain 055   . . . . . . . . . . . . . . . . . . . . . . . . . . . . . . . . . . . . . . . . T . . . . . . . . . . . . . . . . . . . . . . . . . . . .
```

Fig. 7

```
                    10         20         30         40         50         60         70         80         90
                    |          |          |          |          |          |          |          |          |
SEQ ID NO: 29       CGAGCTGGGGCAGGGACGGCTGACTGGGTGCCAAACTTCGACGGCACTTTGCAGGAGCCGAAAATGTACCTGCCCGTCTGCCAAACATT
SEQ ID NO: 3   SHBO 35964        . . . . . . . . . . . . . . . . . . . . . . . . . . . . . . . . . . . . . . . . . T . . . . . . . . . . . . . . . . . . . . . . . . . . . .
```

Fig. 8

```
                    10         20         30         40         50         60         70         80         90
                    |          |          |          |          |          |          |          |          |
SEQ ID NO: 30       TGCCGTGAAGTGGCTCAGGCGGCAATCGCATTAATCGACCAGCAGCCGAAAACCACGCTTGATCAGCTGTGGATATCGTGCAGGGGCCCGGATTATCCG
SEQ ID NO: 4   SHFL 29903        . . A . . . . . . . . . . . . . . . . . . . . . . . . . . . . . . . . . . . . . . . . . . . . . . T . . . . . . . . . . . . . . . . . . . . . . . . . . . .
```

Fig. 9

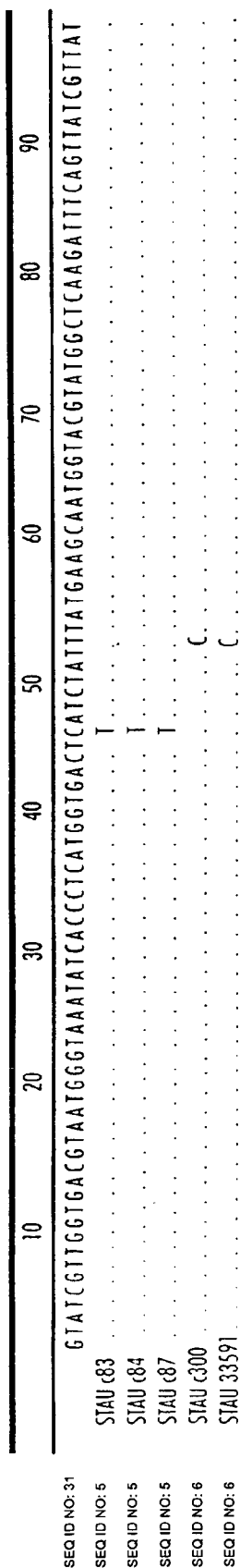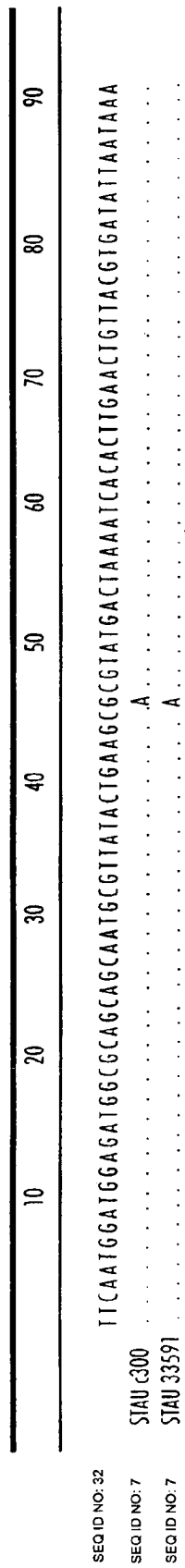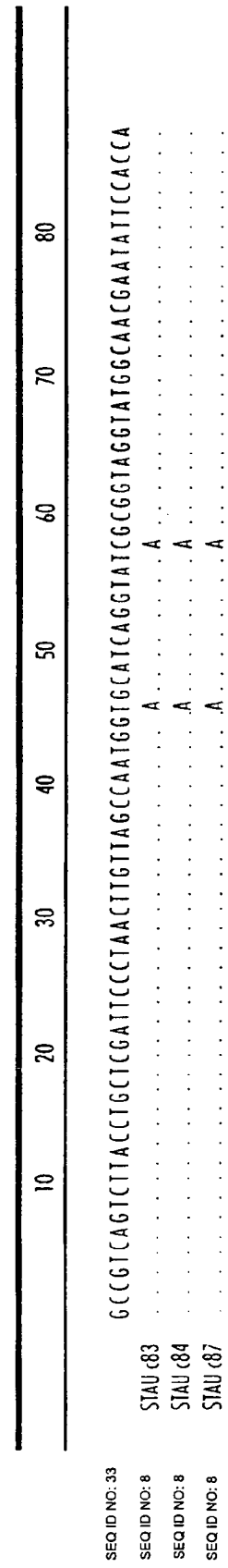

Fig. 11

```
     10        20        30        40        50        60        70        80        90        100
T(GTACGCTGCTGTTGACTTCTTATCGTCAGATGCCCGAAATCGTTGAACATCGTTACATCGTCAGCGCCGCCGCTGTACAAAGTGAAGAAAGG    SEQ ID NO: 34
.............................................T................................................    SEQ ID NO: 9
...........................T....................................................................    SEQ ID NO: 37
```

Fig. 12

```
     10        20        30        40        50        60        70        80        90
ACTGTACCTGGTGGAAGGGGACTCCGCGGGCGGCCTCTGCAAGGCGCGTAACGCAAGAACCAGGCGGATTCTGCCGCTGAAGGGTAAAATCCT    SEQ ID NO: 35
...............................A...............................................................    SEQ ID NO: 10
............................C....................................................................    SEQ ID NO: 11
```

Fig. 13

```
     10        20        30        40        50        60        70        80        90
AACCGCAAGAACCAGGCGGATTCTGCCGCTGAAGGGTAAAATCCTCAACGTCGAGAAAGCGGCTTCGATAAGATGCTCTCTTCTCAGGAAG    SEQ ID NO: 36
.........................T.......................................................................    SEQ ID NO: 12
```

TOPOISOMERASE TYPE II GENE POLYMORPHISMS AND THEIR USE IN IDENTIFYING DRUG RESISTANCE AND PATHOGENIC STRAINS OF MICROORGANISMS

FIELD OF THE INVENTION

This invention relates generally to detection of organisms by gene sequence polymorphisms. More specifically, this invention relates to the detection of drug resistance, and differentiation of very closely related microorganisms by detection of novel polymorphisms in topoisomerase gene loci.

BACKGROUND OF THE INVENTION

Pathogenic strains of E. coli are a common target for identification in clinical settings. For example, E. coli O157: H7 is a pathogenic bacterium that causes severe diarrhea, hemorrhagic colitis and hemolytic uremic syndrome (Nataro and Kaper 1988, Whittam 1993). Rapid identification of E. coli O157:H7, other shiga toxin producing E. coli ("STEC"), other entero-pathogenic E. coli (e.g., O26:H11) and non-pathogenic E. coli is critical for proper treatment and control of epidemics (McDonald and Osterholm, 1993, Majkowski, 1997).

Additionally, in connection with identifying such bacteria, there is also interest in discovering which drugs are effective against such microorganisms so that a treatment regimen can be initiated. Many of the current methods that are used to diagnose pathogenic and drug resistant strains of bacteria require the isolation of the suspect sample from bacterial monocultures that must be incubated over a number of days only after which the pathogenic strain can be identified by performance of biochemical tests. (see review in Swaminathan 1994). Such tests include phage typing, sorbitol fermentation, beta-glucuronidase production, protein identification by immunological means, colony hybridization with DNA probes, and restriction fragment length polymorphism ("RFLP") analysis.

Assays incorporating nucleic acid amplification have the potential to lower the costs and shorten considerably the assay time due to the increased organism-specific sensitivity and the ability to identify particular organisms (genera and strains) directly from mixed culture samples. Such shortening of time and lowering of costs will allow patient samples to be tested for the identification of specific pathogenic strains on a routine basis in contrast to the current practice of testing for such organisms on an "as needed" basis.

Numerous nucleic acid based methodologies have been devised for microorganism identification including the use of DNA amplification (see Arbeit 1995, Whelen and Pershing 1996). One method, the random amplification of polymorphic DNA, ("RAPD"), uses a single random primer in a polymerase chain reaction ("PCR") to obtain a fingerprint of random amplification products. The RAPD technique suffers from the need to establish monocultures prior to strain detection and identification. Moreover, the RAPD technique requires the skill of a technician trained to interpret a complex pattern of bands generated by the technique.

Another method targets regions of nucleotide sequence that encode, or are related to the production of, a pathogen's toxin. For example, specific gene loci for shiga toxins, such as slt-I, and slt-II afford the ability to distinguish E. coli O157:H7 from strains of non-toxin producing pathogens. However, the use of toxin specific loci are limited because testing is only applicable to a narrow range of microbial species that encode the specific toxin being tested.

Another bacterial identification system uses 16S-ribosomal RNA (Weisberg et al. 1991, Neefs et al. 1993). The 16S system is less than desirable because multiple copies of the rRNA gene may contain multiple polymorphisms (a situation known as heteroplasmy) making identification of a specific bacterial strain difficult. Additionally, while the system is able to separate unknown bacteria to the species level, it is not possible to differentiate subspecies strains.

Still other methods which use genetic sequences in hybridization oriented identification are documented. In particular, a method of identifying microorganisms using polymorphisms within the type II DNA topoisomerase genes has been disclosed (Annu. Rev. Genet., 1996, Vol. 30, pp 79–107, by W. M. Huang, Antimicrobial Agents and Chemotherapy, September 1995, Vol. 39, No. 9, pp 2145–2149, by I. Guillemin et al., U.S. Pat. No. 5,645,994, by W. M. Huang, all of which are herein incorporated by reference).

Prokaryotic and eukaryotic type II topoisomerases are related in their structure and function. These molecules are essential for maintenance of DNA superhelicity for DNA replication. One type II topoisomerase from bacteria is DNA gyrase. Bacterial DNA Gyrase is composed of two subunits, GyrA and GyrB. The amino acid sequence of the GyrA subunit is highly conserved between prokaryotic and eukaryotic organisms. However, at the DNA level codon usage and G-C content are markedly divergent. The divergence in the nucleic acid sequences has provided the basis for the development of rapid methodology to identify new bacterial topoisomerase genes (see W. M. Huang 1996).

Comparison of a variety of prokaryotic Gyrase A genes shows that the length of the protein encoded by such genes is in the range of 850 amino acids. The overall identity among GyrA proteins from these different organisms is only about 40% with the greatest variability occurring in the C-terminal third of the sequences. However, the N-terminal portion of the genes are highly conserved, which conservation allows the grouping of the various species in a manner consistent with the grouping elucidated using rRNA sequence analysis. (see Neef, 1993, and Olsen, 1994).

The known GyrB subunit gene sequences encode proteins of between 650 and 800 amino acids in length. In general, the GyrB proteins from various organisms tested share approximately 60% overall amino acid sequence identity.

A second type II topoisomerase gene known in E. coli has sequence identity with the GryA. Specifically, the parC gene has 36% identity with and is generally shorter than the GryA gene encoding a protein of about 750 amino acids.

Alignment of type II topoisomerase genes from a variety of organisms has revealed that the N-terminal region is highly conserved at the amino acid level such that there are at least nine regions having at least five invariant amino acids interspersed with more variable regions. The consensus regions provide DNA sequences that are useful for designing "universal" primers for the amplification of intervening variable regions. The availability of nucleic acid sequences of the intervening variable regions has allowed identification of new topoisomerase genes in such organisms and consequently the ability to study biodiversity at the species level.

For example, U.S. Pat. No. 5,645,994 by W. M. Huang discloses a method of identifying species of bacteria by amplifying variable or "signature" sequences that are interspersed between the conserved sequences. The flanking conserved sequences are used to design universal primers for amplification of the signature sequences. Following amplification, the signature sequences are cloned and sequenced and the sequence is compared against a database of signature sequences from multiple species. Likewise, Huang discloses that alignment of the DNA sequences from isolates of one genus can be used to examine micro-diversity among species of a genus.

The current invention provides numerous polymorphisms recently discovered in the GyrA, GyrB, and parC subunits of topoisomerase type II genes that have application in the detection and identification of subspecies of pathogenic and nonpathogenic bacteria. The current invention also provides polymorphisms identified in the type II isomerases that are associated with drug resistance wherein the proteins and regulation of the genes in which the polymorphisms are found are not affected by or biochemically associated with the function of the drug.

For example, with regard to drug resistance, outbreaks of drug resistant strains of *Staphylococcus aureus* occur periodically in clinical environments such as in hospitals where there may be concentrations of patients suffering from compromised immune systems (Herwaldt and Wenzel 1995). Rapid identification of such resistant strains is recognized as being crucial for the adoption of appropriate treatment regimens (Morita 1993). Most important in such resistance outbreaks has been resistance to methicillin. With respect to methicillin resistance, a gene locus frequently responsible for such resistance is the mecA locus (see Archer and Neimeyer 1994) which has been, along with surrounding noncoding regions, the target of amplification-based assays (e.g., Murakami et al. 1991). While the mecA gene provides a direct link to methicillin resistance, the locus is specific to the genus *Staphylococcus* and thus is of limited utility as a general diagnostic because only drug resistant *Staphylococcus aureus* should be identified. Moreover, because mecA DNA is susceptible to horizontal transfer between bacteria, (Archer and Niemeyer 1994, Wu et al. 1996), the potential for misidentification exists causing serious drawbacks to the use of mecA as an identification marker for pathogenic *S. aureus*.

In contrast, topoisomerase type II polymorphisms have been used to identify drug resistance in microorganisms. Specifically, the Gryase A gene has been used to study resistance of certain bacterial strains to fluoroquinolone ("FQ") antibiotics. (e.g., *Mycobacterium* sp. Guillemin 1995, *Campylobacter* sp. and *Helicobacter* sp. Husmann 1997, and *Staphylococcus aureus* Wang 1998). Biochemically, FQ resistance functions because the mutation in the GyrA protein sequence interferes with the ability of the antibiotic to interact with GyrA/DNA complexes resulting in continued growth and division of the replicating organism. It has been observed that the mutations responsible for FQ resistance are clustered within a small pocket of amino acids in the N-terminal portion of the protein. Since the biochemistry and the genetics of the GyrA gene suggest the involvement of a small number of amino acids, the amino acids at these positions can be correlated with the general antibiotic susceptibility of these bacteria. Thus, as suggested by Guillemin, a screening method may be developed to identify species having resistance to FQ antibiotics based on the mutations in the Gyrase A gene.

Of greater significance, we have discovered polymorphisms in the Gyrase A gene that are associated with non-FQ antibiotics drug resistance that is not involved in or associated with the functionality of topoisomerase:DNA complexes. This discovery is very important because it indicates that polymorphisms in the GyrA subunit are indicative of subtle but distinct differences between organisms where there is no known evolutionary pressure that would assist an organism in developing such genetic divergence.

Although the prior disclosures are directed to the use of Gyrase A gene polymorphisms in the identification of species of organisms and at least one class of antibiotic resistance, such prior disclosures have failed to recognize or disclose a recognizable association between topoisomerase type II sequence polymorphisms and significant divergence between very closely related organisms. For example, pathogenic strains of *E. coli* that have been isolated and classified as strain 0157:H7 have been found to include numerous polymorphisms. Thus, it is questionable whether classifying such isolates as only one strain (i.e. 0157:H7) is satisfactory. Likewise, it has been found that *E. coli* strain K12, which has traditionally been attributed to be the same strain as wild type *E. coli* ATCC 11775, is divergent from the wild type strain and is actually a separate "laboratory" strain as indicated by divergence in the Gyrase A gene. (see below)

The current invention recognizes the importance of these subtle divergences within the GyrA, GyrB, and parC proteins of the topoisomerase family and provides numerous polymorphisms useful for the identification of closely related organisms that may be heretofore unrecognized subspecies variations within populations of organisms that have traditionally been classified together as a single species.

SUMMARY OF THE INVENTION

The current invention provides numerous polymorphisms in the topoisomerase type II loci gyrA, gyrB, and parC, that have been identified in a variety of microorganisms and that are useful as identification markers for distinguishing pathogenic from non-pathogenic as well as drug resistant from non-drug resistant organisms. In one embodiment of the invention, point mutations are disclosed within a 100 base-pair N-terminal fragment of the Gyrase A gene.

In a preferred embodiment one point mutation for a set of organisms (e.g., *E. coli* strains 0157:H7, 055:K59(B5):H—) may be found within a 91 base-pair fragment of the GyrA gene which begins at codon 69 and ends at codon 99. More specifically, this point mutation is a guanine to adenine (G to A) substitution in the third position of codon 84.

In another preferred embodiment one point mutation for a set of organisms (e.g., *E. coli* strains 0157:H7, 055:K59 (B5):H—) may be found within a 102 base-pair fragment of the GyrB gene which begins at codon 236 and ends at codon 270. More specifically, this point mutation is a cytosine to thymine (C to T) substitution in the third position of codon 251.

In another preferred embodiment one point mutation for a set of organisms (e.g., *Shigella boydii*) may be found within a 96 base-pair fragment of the GyrB gene which begins at codon 149 and ends at codon 181. More specifically, this point mutation is a thymine to cytosine (T to C) substitution in the third position of codon 166.

In another preferred embodiment one point mutation for a set of organisms (e.g., *Shigella sonnei*) may be found within a 96 base-pair fragment of the GyrB gene which begins at codon 149 and ends at codon 181. More specifically, this point mutation is a guanine to adenine (G to A) substitution in the third position of codon 164.

In another preferred embodiment one point mutation for a set of organisms (e.g., *Shigella flexneri*) may be found within a 91 base-pair fragment of the GyrB gene which begins at codon 167 and ends at codon 197. More specifically, this point mutation is a cytosine to thymine (C to T) substitution in the third position of codon 181.

In another preferred embodiment one point mutation for a set of organisms (e.g., *E. coli* strains 0157:H7, 055:K59 (B5):H—) may be found within a 91 base-pair fragment of the parC gene which begins at codon 121 and ends at codon 151. More specifically, this point mutation is a cytosine to thymine (C to T) substitution in the first position of codon 136.

In another preferred embodiment one point mutation for a set of organisms (e.g., *Shigella boydii* isolate ATCC 35964) may be found within a 91 base-pair fragment of the parC gene which begins at codon 134 and ends at codon 164. More specifically, this point mutation is a cytosine to thymine (C to T) substitution in the third position of codon 149.

In another preferred embodiment one point mutation for a set of organisms (e.g., *Shigella flexneri* isolate 29903) may be found within a 95 base-pair fragment of the parC gene which begins at codon 185 and ends at codon 216. More specifically, this point mutation is a cytosine to thymine (C to T) substitution in the third position of codon 201.

In yet another preferred embodiment one point mutation for a set of organisms having resistance to methicillin, (e.g., Sharp Memorial Hospital *Staphylococcus aureus* isolates C83, C84, and C87) may be found within a 98 base-pair fragment of the GyrA gene which begins at codon 69 and ends at codon 101. More specifically, this point mutation is a cytosine to thymine (C to T) substitution in the second position of codon 84.

In yet another preferred embodiment one point mutation for a set of organisms having resistance to methicillin, (e.g., Sharp Memorial Hospital *Staphylococcus aureus* isolates C300, and ATCC 33591) may be found within a 98 base-pair fragment of the GyrA gene which begins at codon 69 and ends at codon 101. More specifically, this point mutation is a thymine to cytosine (T to C) substitution in the third position of codon 86.

In yet another preferred embodiment one point mutation for a set of organisms having resistance to methicillin, (e.g., Sharp Memorial Hospital *Staphylococcus aureus* isolates C300, and ATCC 33591) may be found within a 91 base-pair fragment of the GyrA gene which begins at codon 112 and ends at codon 142. More specifically, this point mutation is a guanine to adenine (G to A) substitution in the third position of codon 127.

In still another preferred embodiment one point mutation for a set of organisms having resistance to methicillin, (e.g., Sharp Memorial Hospital *Staphylococcus aureus* isolates C83, C84, and C87) may be found within a 88 base-pair fragment of the GyrA gene which begins at codon 157 and ends at codon 186. More specifically, this point mutation is a thymine to adenine (T to A) substitution in the third position of codon 172.

In still another preferred embodiment one point mutation for a set of organisms having resistance to methicillin, (e.g., Sharp Memorial Hospital *Staphylococcus aureus* isolates C83, C84, and C87) may be found within a 88 base-pair fragment of the GyrA gene which begins at codon 157 and ends at codon 186. More specifically, this point mutation is a cytosine to adenine (C to A) substitution in the third position of codon 176.

Other preferred embodiments relate to the manner in which the point mutations may be used to identify organisms.

In one embodiment, the mutant sequence may be incorporated into oligonucleotide probes for use in restriction fragment length polymorphism ("RFLP") analysis.

In another embodiment, probes may be designed which incorporate the mutations for use in strain-specific DNA amplification. In this embodiment, oligomers are designed such that the nucleotide of the point mutation is placed at the 3' terminal portion of the oligomer. This allows the use of techniques in which amplification will occur only if the point mutation is present in the organism being tested.

In another embodiment, probes incorporating the point mutations are provided for use either as labeled signal probes or as capture probes in conjunction with microelectronic assay formats.

In still another embodiment the identified gene fragments containing the polymorphisms provide nucleic acid sequences for designing oligonucleotide primers for nucleic acid amplification.

BRIEF DESCRIPTION OF THE DRAWINGS

FIG. 6 is a DNA sequence identity chart showing a lineup of the nucleic acid sequence in the GyrA gene showing the location and sequence of each of the polymorphisms in GyrA disclosed herein in for *E. coli* strains O157H:7, and O55:K59(B5):H— corresponding to I of FIG. 1. The polymorphism of import is a G to A transition (Seq. Id. No. 1). The figure also denotes two other polymorphisms of a C to T transition which are not associated with pathogenicity. The mutant sequence is compared to wild type *E. coli* strain K-12 (Seq. Id. No. 27).

FIG. 7 is a DNA sequence identity chart showing a lineup of the nucleic acid sequence in the parC gene showing the location and sequence of each of the polymorphisms (Seq. Id. No. 2) in parC disclosed herein for *E. coli* strains O157H:7, and 055:K59(B5):H— corresponding to II of FIG. 2. The mutant sequence is compared to wild type strain K-12 (Seq. Id. No. 28).

FIG. 8 is a DNA sequence identity chart showing a lineup of the nucleic acid sequence in the parC gene showing the location and sequence of each of the polymorphisms (Seq. Id. No. 3) in parC disclosed herein for *Shigella boydii* isolates CDC 2710-54 (ATCC 35964) corresponding to III of FIG. 2. The mutant sequence is compared to wild type *E. coli* strain K-12 (Seq. Id. No. 29).

FIG. 9 is a DNA sequence identity chart showing a lineup of the nucleic acid sequence in the parC gene showing the location and sequence of the polymorphisms (Seq. Id. No. 4) in parC disclosed herein for *Shigella flexneri* isolate ATCC 29903 corresponding to UV in FIG. 2. The mutant sequence is compared to wild type *E. coli* strain K-12 (Seq. Id. No. 30).

FIG. 10a is a DNA sequence identity chart showing a lineup of the nucleic acid sequence in the GyrA gene showing the location and sequence of each of the polymorphisms in the MRSA I section of GyrA disclosed herein for *Staphylococcus aureus* isolates C83, C84, and C87 (Seq. Id. No. 5); and ATCC 33591 and C300 (Seq. Id. No. 6) which are associated with drug resistance. This sequence corresponds to MSRA I of FIG. 3. The polymorphic sequence is compared against non-methicillin resistant *S. aureus* Genebank sequence M86227 (Seq. Id. No. 31).

FIG. 10b is a DNA sequence identity chart showing a lineup of the nucleic acid sequence in the GyrA gene showing the location and sequence of each of the polymorphisms (Seq. Id. No. 7) in the MRSA II section of GyrA disclosed herein for *Staphylococcus aureus* isolates ATCC 33591, and C300 which are associated with drug resistance. This sequence corresponds to MSRA II of FIG. 3. The polymorphic sequence is compared against non-methicillin resistant *S. aureus* Genebank sequence M86227 (Seq. Id. No. 32).

FIG. 10c is a DNA sequence identity chart showing a lineup of the nucleic acid sequence in the GyrA gene showing the location and sequence of each of the polymorphisms (Seq. Id. No. 8) in the MRSA III section of GyrA disclosed herein for *Staphylococcus aureus* isolates C83, C84, C87 which are associated with drug resistance. This sequence corresponds to MSRA III of FIG. 3. The polymorphic sequence is compared against non-methicillin resistant *S. aureus* Genebank sequence M86227 (Seq. Id. No. 33).

FIG. 11 is a DNA sequence identity chart showing a lineup of the nucleic acid sequence in the GyrB gene showing the location and sequence of each of the polymorphisms (Seq. Id. Nos. 9 and 37) in GyrB disclosed herein for *E. coli* strains 0157:H7 and 055:K59(B5):H—. The polymorphic sequence is compared against *E. coli* strain K-12 M61655 (Seq. Id. No. 34).

FIG. 12 is a DNA sequence identity chart showing a lineup of the nucleic acid sequence in the GyrB gene showing the location and sequence of each of the polymorphisms in GyrB disclosed herein for *Shigella boydii* isolate ATCC 35964 (Seq. Id. No. 10) and *Shigella sonnei* isolate 29930 (Seq. Id. No. 11). The polymorphic sequence is compared against *E. coli* strain K-12 (Seq. Id. No. 35).

FIG. 13 is a DNA sequence identity chart showing a lineup of the nucleic acid sequence in the GyrB gene showing the location and sequence of each of the polymorphisms (Seq. Id. No. 12) in GyrB disclosed herein for *Shigella flexneri*. The polymorphic sequence is compared against *E. coli* strain K-12 (Seq. Id. No. 36).

DETAILED DESCRIPTION OF THE INVENTION

Figure 1:
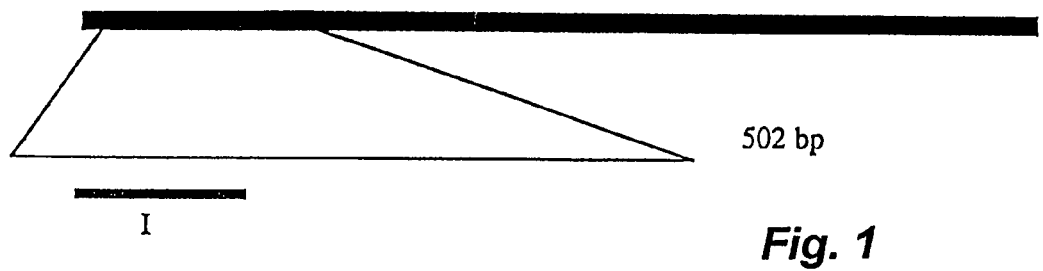
FIG. 1 is a schematic diagram showing the relative position (i.e., I) of the 30 nucleic acid fragment containing the polymorphism in the GyrA gene related to identification of pathogenic *E. coli* strain O157:H7
Figure 2:
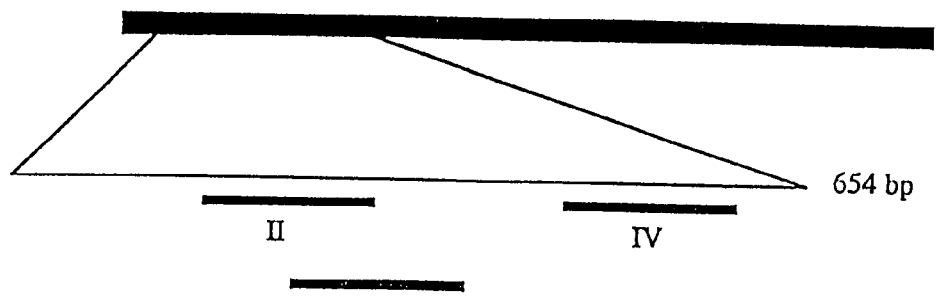
FIG. 2 is a schematic diagram showing the relative positions of the nucleic acid fragments containing the polymorphisms in the parC gene related to identification of pathogenic *E. coli* strain O157:H7 (i.e., II); identification of pathogenic *Shigella boydii* (i.e., III), and identification of pathogenic *Shigella flexneri* (i.e., IV).
Figure 3:
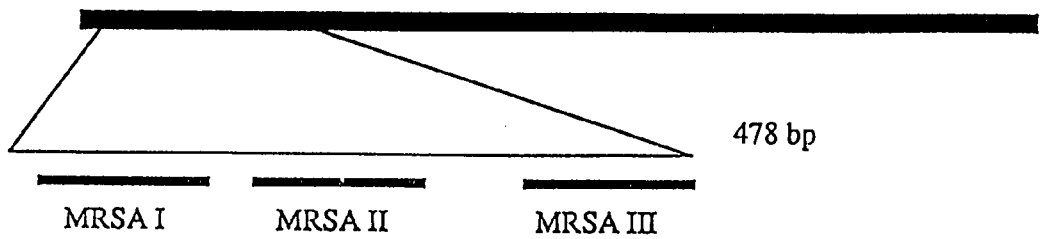
FIG. 3 is a schematic diagram showing the relative positions of the nucleic acid fragments containing the polymorphisms in the GyrA gene related to identification of methicillin resistance in *Staphylococcus aureus* (i.e., Gyr A sections MRSA I, MRSA II, and MRSA III).
Figure 4:
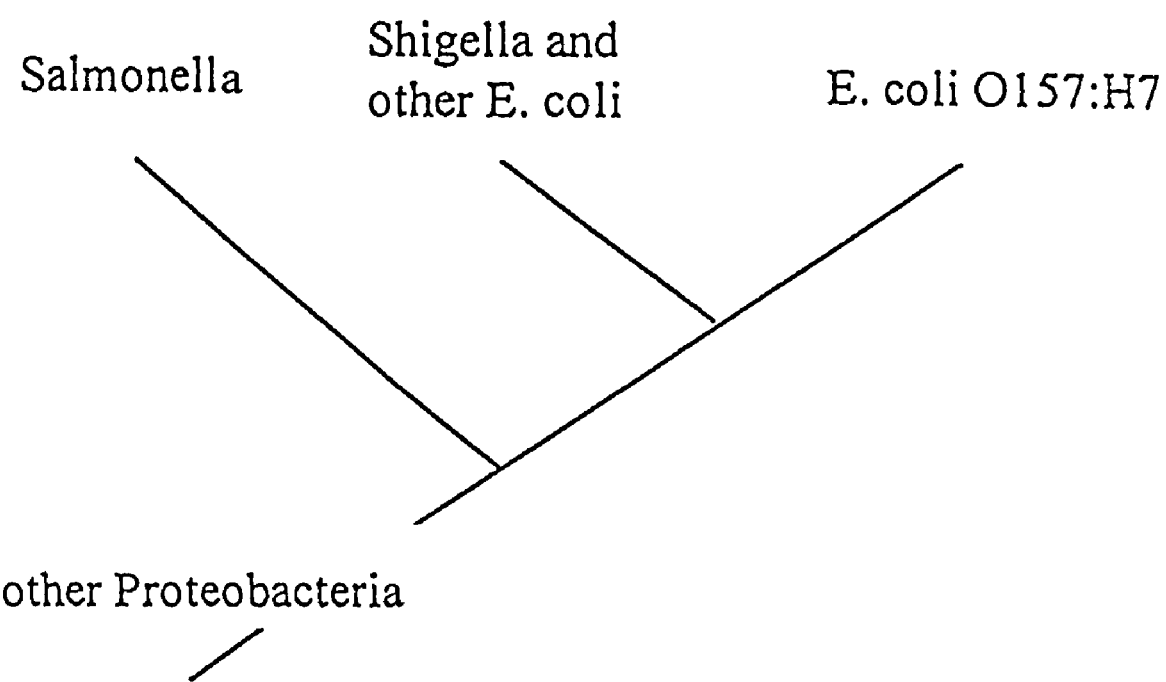
FIG. 4 is an evolutionary lineage diagram indicating that, as indicated by the polymorphisms associated with the pathogenic *E. coli* strain O157:H7, the O157:H7 strain is an independent evolutionary lineage from *Shigella* sp. and other *E. coli*.
Figure 5:
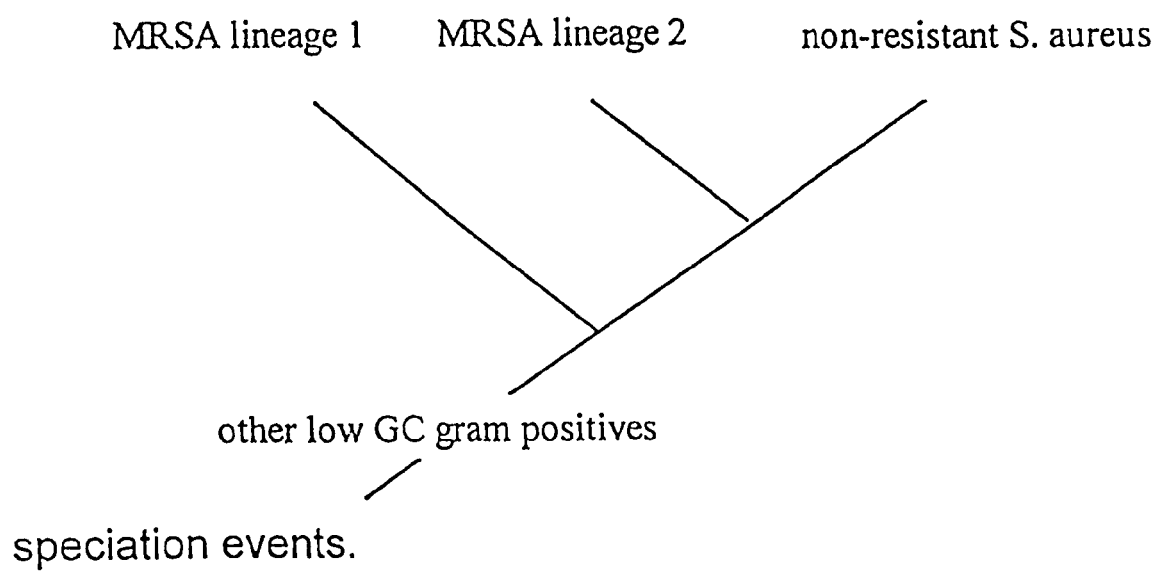
FIG. 5 is an evolutionary lineage diagram indicating that, as indicated by the two sets of polymorphisms for *S. aureus* isolates C83, C84, and C87 versus wild type isolates of *S. aureus* ATCC 33591 and C300, the polymorphisms may represent speciation events.

The present invention provides sets of point mutations or polymorphisms within the topoisomerase II subunit-encoding genes of the GyrA, GyrB, and parC loci. These polymorphisms allow the identification of *E. coli* O157:H7, *Shigella flexneri*, *S. sonnei*, *S. boydii*, and methicillin resistant *Staphylococcus aureus*.

The present invention further provides regions of nucleic acid sequences within the topoisomerase II subunit-encoding genes (i.e. GyrA, GyrB, and parC) that flank the identified polymorphisms and are useful for designing amplification-primers that can be used in the identification of pathogenic and drug resistant strains of microorganisms. These primer sequences are in some cases contiguous with (i.e. adjacent to) the identified polymorphisms and may, in some instances, include within the primer sequence the identified polymorphisms.

The present invention further provides amplification-primer sequences within the topoisomerase II subunit-encoding genes for GyrA that flank the identified polymorphisms associated with methicillin resistance in strains of *Staphylococcus aureus*.

The location of specific polymorphisms associated with particular organisms and which comprise embodiments of the invention are as follows:

(1) In *E. coli* strain O157:H7 and 055:K59(B5):H—, as compared to nonpathogenic *E. coli* strain K12, a polymorphism is located within a 91 base-pair region of the GyrA gene starting from position 3 of codon 69 to position 3 of codon 99. The relevant polymorphism is a guanine (G) to adenine (A) substitution in the third position of codon 84. (Seq. Id. No. 1) FIG. 6.

(2) In *E. coli* strains O157:H7 and 055:K59(B5)H— as compared to nonpathogenic *E. coli* strain K-12, a polymorphism is located within a 102 base-pair region of the GyrB gene starting from position 3 of codon 236 to position 2 of codon 270. The relevant polymorphism is a cytosine (C) to a thymine (T) substitution in the third position of codon 251 (Seq. ID. Nos. 9 and 37) FIG. 11.

(3) In *Shigella boydii*, isolate ATCC 35964, as compared to nonpathogenic *E. coli* strain K-12, a polymorphism is located within a 96 base-pair region of the GyrB gene starting from position 3 of codon 149 to position 2 of codon 181. The relevant polymorphism is a thymine (T) to a cytosine (C) substitution in the third position of codon 166. (Seq. Id. No. 10) FIG. 12.

(4) In *Shigella sonnei*, isolate ATCC 29930, as compared to nonpathogenic *E. coli* strain K-12, a polymorphism is located within a 96 base-pair region of the GyrB gene starting from position 3 of codon 149 to position 2 of codon 181. The relevant polymorphism is a guanine (G) to adenine (A) substitution in the third position of codon 164. (Seq. Id. No. 11) FIG. 12.

(5) In *Shigella flexneri*, as compared to nonpathogenic *E. coli* strain K-12, a polymorphism is located within a 91 base-pair region of the GyrB gene starting from position 1 of codon 167 to position 3 of codon 197. The relevant polymorphism is a cytosine (C) to a thymine (T) substitution in the third position of codon 181. (Seq. Id. No. 12) FIG. 13.

(6) In *E. coli* strain O157:H7 and 055:K59(B5):H—, as compared to nonpathogenic *E. coli* strain K12, a polymorphism is located within a 91 base-pair region of the parC gene starting from position 1 of codon 121 to position 1 of codon 151. The relevant polymorphism is a cytosine (C) to a thymine (T) substitution in the first position of codon 136. (Seq. Id. No. 2) FIG. 7.

(7) In *Shigella boydii*, isolate ATCC 35964, as compared to nonpathogenic *E. coli* strain K12, a polymorphism is located within a 91 base-pair region of the parC gene starting from position 3 of codon 134 to position 3 of codon 164. The relevant polymorphism is a cytosine (C) to a thymine (T) substitution in the third position of codon 149. (Seq. Id. No. 3) FIG. 8.

(8) In *Shigella flexneri*, isolate ATCC 29903, as compared to nonpathogenic *E. coli* strain K12, a polymorphism is located within 95 base-pair region of the parC gene starting from position 2 of codon 185 to position 3 of codon 216. The relevant polymorphism is a cytosine (C) to a thymine (T) substitution in the third position of codon 201. (Seq. Id. No. 4) FIG. 9.

(9) In *Staphylococcus aureus*, isolates C83, C84, and C87, as compared to non-methicillin resistant *S. aureus* Genebank sequence M86227, a polymorphism is located within a 98 base-pair regions of the GyrA gene starting from position 2 of codon 69 to position 3 of codon 101. The relevant polymorphism is a cytosine (C) to thymine (T) substitution in the second position of codon 84. (Seq. Id. No. 5) FIG. 10*a*.

(10) In *Staphylococcus aureus*, isolates C300 and ATCC 33591, as compared to non-methicillin resistant *S. aureus* Genebank sequence M86227, a polymorphism is located within a 98 base-pair regions of the GyrA gene starting from position 2 of codon 69 to position 3 of codon 101. The relevant polymorphism is a thymine (T) to cytosine (C) substitution in the third position of codon 86. (Seq. Id. No. 6) FIG. 10*a*.

(11) In *Staphylococcus aureus*, isolates C300 and ATCC 33591, as compared to non-methicillin resistant *S. aureus* Genebank sequence M86227, a polymorphism is located within a 91 base-pair regions of the GyrA gene starting from position 3 of codon 112 to position 3 of codon 142. The relevant polymorphism is a guanine (G) to adenine (A) substitution in the third position of codon 127. (Seq. Id. No. 7) FIG. 10*b*.

(12) In *Staphylococcus aureus*, isolates C83, C84, and C89, as compared to non-methicillin resistant *S. aureus* Genebank sequence M86227, a polymorphism is located within a 88 base-pair regions of the GyrA gene starting from position 3 of codon 157 to position 3 of codon 186. The relevant polymorphism is a thymine (T) to adenine (A) substitution in the third position of codon 172. (Seq. Id. No. 8) FIG. 10*c*.

(13) In *Staphylococcus aureus*, isolates C83, C84, and C89, as compared to non-methicillin resistant *S. aureus* Genebank sequence M86227, a polymorphism is located within a 88 base-pair regions of the GyrA gene starting from position 3 of codon 157 to position 3 of codon 186. The relevant polymorphism is a cytosine (C) to adenine (A) substitution in the third position of codon 176. (Seq. Id. No. 8) FIG. 10*c*.

The invention contemplates that the identified polymorphisms can be used in a variety of ways. In one embodiment, they are incorporated into oligonucleotide probes for use in RFLP analysis or hybridization experiments. In a second embodiment, the polymorphisms are used in identifying strains by nucleic acid amplification techniques. Techniques for amplification of nucleic acid sequences are well known in the art and include such procedures as polymerase chain reaction (PCR), reverse transcription PCR, and strand displacement amplification (SDA). In a third embodiment, the polymorphisms may be incorporated in capture and capture mediator probes for use in conjunction with electronic microchip hybridization platforms. The uses as disclosed are not meant to be exclusive and, as one skilled in the art will recognize, the disclosed uses are only meant to represent characteristic examples of how the point mutations can be used in diagnostic assays.

Example I

Figure 14:
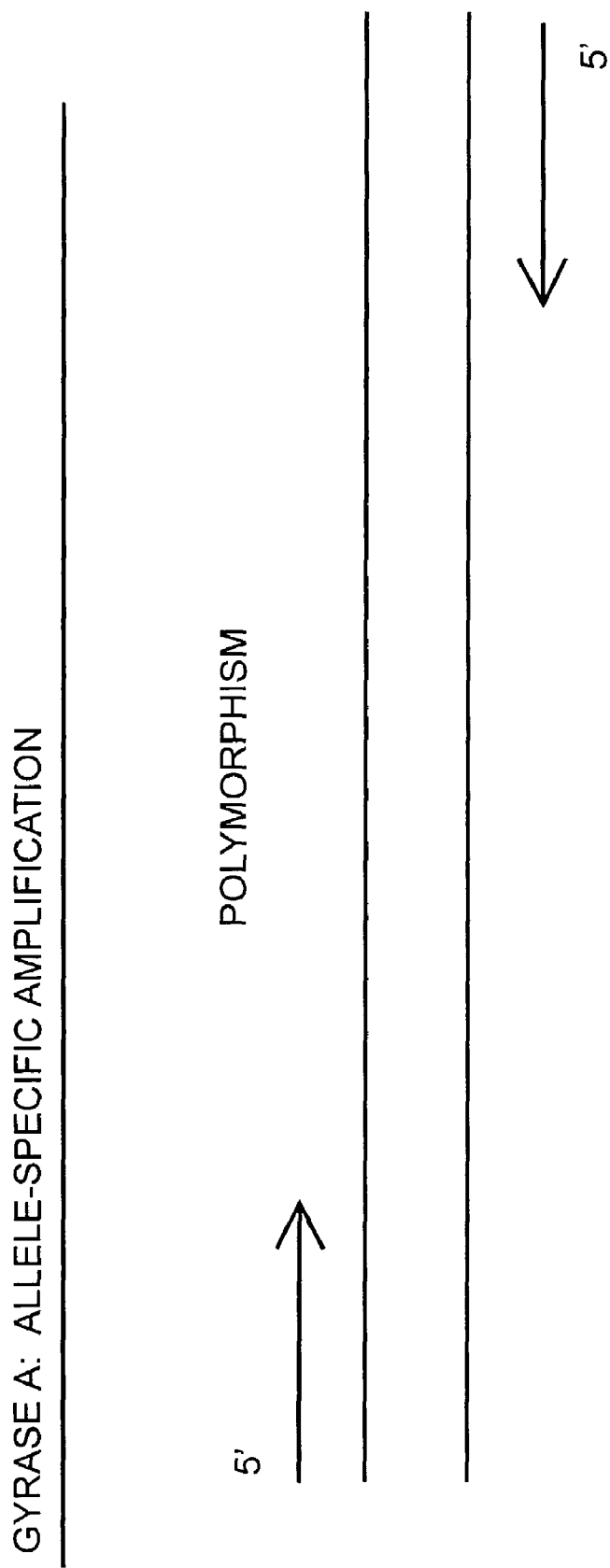
FIG. 14 is a schematic of one embodiment of how the polymorphisms disclosed herein can be used in nucleic acid amplification techniques to identify the presence of the polymophism.
Figure 15:
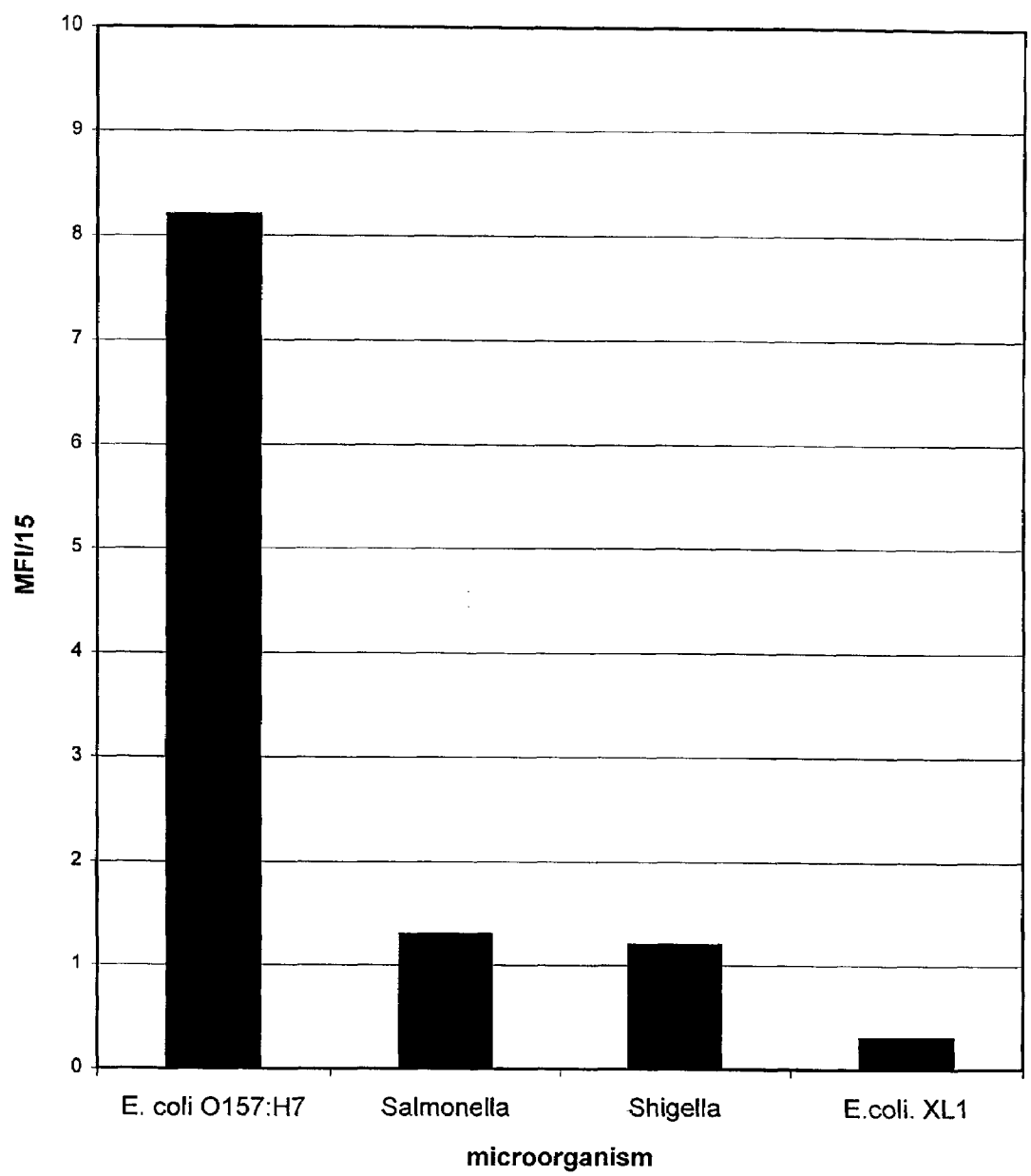
FIG. 15 depicts the results of amplification following the scheme represented in FIG. 14.

In one embodiment, amplification of nucleic acids containing a polymorphism can be carried out. For example, some polymorphisms comprise multiples of point mutations in the topoisomerase genes. As schematically diagramed in FIG. 14, oligonucleotide primers to be used in such an amplification reaction are designed so that at least one primer has at the respective 3' terminal base a nucleotide that is complementary to a single polymorphism (i.e. mutation) base of one strand of the gene. Designing the primer to have the 3' base complement a specific polymorphism will allow detection of the polymorphism by the amplification of the sequence bounded by the primers (if complementation occurs), or the detection of the absence of the polymorphism by the non-amplification of the sequence bounded by the primers (if complementation does not occur). The possibility for such detection is due to the well known phenomenon that extension and amplification is unfavored where the 3' base of the amplification primer is mismatched to the template sought to be amplified. Thus, if the mutation is present in the sample, the primers will be extended to produce amplified sequence bracketed by the primers. Conversely, if the mutation in the test sample is not present, the primers will be ineffective as amplification primers. The technique is equally applicable in reverse in that at least one of the 3' bases may be complimentary to the wild type sequence wherein amplification will occur only if the wild type sequence is present whereas if the polymorphism is present, no amplification will be observed.

For example, Seq. Id. No. 13 incorporating the polymorphism base on the 3' end can be used with Seq. Id. No. 14 (designed from the 3'end of the 98 base fragment containing the polymorphism) (FIG. 10*a*) to amplify a short fragment within the 98 base fragment which will contain the polymorphism associated with methicillin resistant *S. aureus* isolates C83, C84, and C87. No amplification will occur unless the polymorphism is present.

Seq. Id. No. 13 5' CACCCTCATGGTGACTT3'

Seq. Id. No. 14 5' ATAACGATAACTGAAATC 3'

The 3' base of Seq. Id. No. 13 is complementary to the mutant polymorphism at codon 84, while the 3' base of Seq. Id. No. 14 is complementary to the wild type sequence at codon 96.

Alternatively, instead of Seq. Id. No. 14, Seq. Id. No. 15 may be used with Seq. Id. No. 13.

Seq. Id. No. 15 5'CGTTGCCATACCTACCGCT 3'

In this instance, Seq. Id. No. 15 has a 3' base that is complementary to the mutant polymorphism at position 176. (FIG. 10*c*) Amplification of the sequence intervening that flanked by sequences 13 and 15 will allow additional observation of the polymorphism at codon position 172 by either sequencing the amplified segment or performing an additional amplification reaction using Seq. Id. Nos. 13 with 16 on the segment that was amplified using Seq. Id. Nos. 13 and 15. Seq. Id. No. 16 contains a base complementary to a polymorphism specific for methicillin drug resistance at the 3' terminus of this primer. for the polymorphism at codon 172. (FIG. 10c)

Seq. Id. No. 16 5' CCGCTATACCTGATGCT 3'

Specific reaction conditions and related amplification methodology is routine and well understood in the art whether using polymerase chain reaction ("PCR") amplification or another amplification technique.

Example II

Methicillin resistant *S. aureus* isolates C300 and ATCC 33591 can be detected using oligonucleotid primers Id. Seq. Nos. 17 and 18.

Seq. Id. No. 17 5'GGTGACTCATCTATC3'

Seq. Id. No. 18 5'ATTTTAGTCATACGT3'

Primer 17 has a 3' base that is the polymorphism at position 3 of codon 86 of GyrA (FIG. 10a) while primer 18 is an oligonucleotide having its 3' base complementary to the polymorphism at position 3 of codon 127 of GyrA (FIG. 10b).

Example III

Pathogenic strains of *E. coli* O157:H7 and O55:K59(B5):H— having polymorphisms in the parC gene may be identified using hybridization techniques and the oligonucleotide sequence Id. No. 19. (FIG. 7)

Seq. Id. No. 19 5'GCGAGTTGGGGCA3'

Pathogenic strains of *Shigella boydii* isolate 35964 having polymorphisms in the parC gene may be identified using hybridization techniques and the oligonucleotide sequence Id. No. 20. (FIG. 8)

Seq. Id. No. 20 5'CGACGGTACTTTGC3'

Pathogenic strains of *Shigella flexneri* isolate 29903 having polymorphisms in the parC gene may be identified using hybridization techniques and the oligonucleotide sequence Id. No. 21. (FIG. 9)

Seq. Id. No. 21 5'CCGAAAACTACGCTC3'

Example IV

Pathogenic strains of *E. coli* O157:H7 and O55:K59(B5):H—, *Shigella boydii* isolate 35964, *Shigella sonnei* isolate 29930, and *Shigella flexneri* having polymorphisms in the GyrB gene may be identified using hybridization techniques and the oligonucleotide sequences Id. Nos. 22 through 25 respectively. (FIGS. 11, 12, 25 and 13)

Seq. Id. No. 22 5'CCGGAAATTGTTGAAC3'

Seq. Id. No. 23 5'GGCGCAACCGCAA3'

Seq. Id. No. 24 5'GCGAAGCAAGGGC3'

Seq. Id. No. 25 5'AAAATCCTTAACGTCG3'

Example V

Pathogenic strains of *E. coli* O157:H7 and O55:K59(B5):H— having polymorphisms in the GyrA gene may be identified using hybridization techniques and the oligonucleotide sequence Id. No. 26. (FIG. 6)

Seq. Id. No. 2 5'ACTCGGCAGTTTATG3'

BRIEF DESCRIPTION OF THE SEQUENCE LISTING

SEQ. ID. No. 1 is a region of the GyrA gene from *E. coli* strains O157:H7 and O55:K59(B5):H— containing a novel polymorphism of an adenine at position 46 of the sequence listed.

SEQ. ID. No. 2 is a region of the parC gene from *E. coli* strains O157:H7 and O55:K59(B5):H— containing a novel polymorphism of a thymine at position 46 of the sequence listed.

SEQ. ID. No. 3 is a region of the parC gene from *Shigella boydii* isolate 35964 containing a novel polymorphism of a thymine at position 45 of the sequence listed.

SEQ. ID. No. 4 is a region of the parC gene from *Shigella flexneri* isolate 29903 containing a novel polymorphism of a thymine at position 45 of the sequence listed.

SEQ. ID. No. 5 is a region of the GyrA gene from *Staphylococcus aureus* isolates C83, C84, and C87 containing a novel polymorphism of a thymine at position 46 of the sequence listed.

SEQ. ID. No. 6 is a region of the GyrA gene from *Staphylococcus aureus* isolates C300, and ATCC 33591 containing a novel polymorphism of a cytosine at position 53 of the sequence listed.

SEQ. ID. No. 7 is a region of the GyrA gene from *Staphylococcus aureus* isolates C300, and ATCC 33591 containing a novel polymorphism of an adenine at position 45 of the sequence listed.

SEQ. ID. No. 8 is a region of the GyrA gene from *Staphylococcus aureus* isolates C83, C84, and C87 containing novel polymorphisms of an adenine at positions 45 and 58 of the sequence listed.

SEQ. ID. No. 9 is a region of the GyrB gene from *E. coli* strains O157:H7 containing a novel polymorphism of a thymine at position 46 of the sequence listed.

SEQ. ID. No. 10 is a region of the GyrB gene from *Shigella boydii* isolate number 35964 containing a novel polymorphism of a cytosine at position 52 of the sequence listed.

SEQ. ID. No. 11 is a region of the GyrB gene from *Shigella sonnei* isolate number 29930 containing a novel polymorphism of an adenine at position 45 of the sequence listed.

SEQ. ID. No. 12 a region of the GyrB gene from *Shigella flexneri* isolate number 29903 containing a novel polymorphism of a thymine at position 45 of the sequence listed.

SEQ. ID. Nos. 13 to 26 are oligonucleotide primers containing a base that is complementary to a polymorphism as disclosed herein or that is within the disclosed region of the gene containing the polymorphism.

SEQ. ID. Nos. 27 to 36 are oligonucleotide sequences of *E. coli* strain K-12.

SEQ. ID. No. 37 is a region of the GyrB gene from *E. coli* strain O55:K59(b5):H— containing a novel polymorphism of a thymine.

The present invention has been described above with reference to preferred embodiments. It would be obvious to one of ordinary skill in the art that many additions, deletions and changes can be made without departing from the spirit and the scope of the invention as claimed below.

What is claimed is:

1. An oligonucleotide selected from the group consisting of SEQ ID Nos.: 15, 16, 17, 18, 19, 20, 21, 22, 23, 24, 25, and 26.

2. A method of detecting methicillin resistant *Staphylococcus aureus* by detecting the presence of at least one polymorphism in a Gyrase A-encoding nucleic acid, the method comprising:

(a) providing a nucleic acid sample obtained from a microorganism;

(b) contacting the sample with at least one forward amplification primer and at least one reverse amplification primer, wherein at least one forward or reverse primer is an oligonucleotide of claim 1 selected from the group consisting of SEQ ID NO. 15, SEQ ID NO. 16, SEQ ID NO. 17, and SEQ ID NO. 18;

(c) amplifying a segment of a Gyrase A-encoding nucleic acid of the sample to form an amplified product, wherein the segment is bounded by the amplification primers; and (d) detecting the presence of the amplified product, wherein the presence of the amplified product indicates that the microorganism is methicillin resistant *Staphylococcus aureus*.

3. A method of detecting methicillin resistant *Staphylococcus aureus* by detecting the presence of at least one polymorphism in a Gyrase A-encoding nucleic acid comprising:

(a) providing a nucleic acid sample obtained from a microorganism;

(b) contacting said sample with at least one oligonucleotide of claim 1 selected from the group consisting of SEQ ID NO. 15, SEQ ID NO. 16, SEQ ID NO. 17, and SEQ ID NO. 18 which has been detectably labeled, under conditions suitable for discerning a single base pair mismatch in the hybridization of the oligonucleotide to a complementary nucleic acid sequence; and (c) detecting hybridization of the labeled oligonucleotide to a Gyrase A-encoding nucleic acid in the sample, wherein the hybridization of the oligonucleotide indicates that the microorganism is methicillin resistant *Staphylococcus aureus*.

* * * * *

SEQUENCE LISTING

<160> NUMBER OF SEQ ID NOS: 37

<210> SEQ ID NO 1
<211> LENGTH: 91
<212> TYPE: DNA
<213> ORGANISM: E. coli

<400> SEQUENCE: 1

```
cgttggtgac gtaatcggta ataccatcc ccatggtgac tcggcagttt atgacacgat      60
cgtccgtatg gcgcagccat tctcgctgcg t                                    91
```

<210> SEQ ID NO 2
<211> LENGTH: 91
<212> TYPE: DNA
<213> ORGANISM: E. coli

<400> SEQUENCE: 2

```
accgaatccc ggttgtcgaa atattccgag ctgctattga gcgagttggg gcaggggacg      60
gctgactggg tgccaaactt cgacggcact t                                    91
```

<210> SEQ ID NO 3
<211> LENGTH: 91
<212> TYPE: DNA
<213> ORGANISM: Shigella boydii

<400> SEQUENCE: 3

```
cgagctgggg caggggacgg ctgactgggt gccaaacttc gacggtactt tgcaggagcc      60
gaaaatgcta cctgcccgtc tgccaaacat t                                    91
```

<210> SEQ ID NO 4
<211> LENGTH: 95
<212> TYPE: DNA
<213> ORGANISM: Shigella flexneri

<400> SEQUENCE: 4

```
tgcgtgaagt agctcaggcg gcaatcgcat taatcgacca gccgaaaact acgctcgatc      60
agctgctgga tatcgtgcag gggccggatt atccg                                95
```

<210> SEQ ID NO 5
<211> LENGTH: 98
<212> TYPE: DNA
<213> ORGANISM: Staphylococcus aureus

<400> SEQUENCE: 5

```
gtatcgttgg tgacgtaatg ggtaaatatc accctcatgg tgacttatct atttatgaag      60
caatggtacg tatggctcaa gatttcagtt atcgttat                             98
```

<210> SEQ ID NO 6
<211> LENGTH: 98
<212> TYPE: DNA
<213> ORGANISM: Staphylococcus aureus

<400> SEQUENCE: 6

```
gtatcgttgg tgacgtaatg ggtaaatatc accctcatgg tgactcatct atctatgaag      60
caatggtacg tatggctcaa gatttcagtt atcgttat                             98
```

<210> SEQ ID NO 7
<211> LENGTH: 91

```
<212> TYPE: DNA
<213> ORGANISM: Staphylococcus aureus

<400> SEQUENCE: 7
ttcaatggat ggagatggcg cagcagcaat gcgttatact gaagcacgta tgactaaaat      60
cacacttgaa ctgttacgtg atattaataa a                                    91

<210> SEQ ID NO 8
<211> LENGTH: 88
<212> TYPE: DNA
<213> ORGANISM: Staphylococcus aureus

<400> SEQUENCE: 8
gccgtcagtc ttacctgctc gattccctaa cttgttagcc aatggagcat caggtatagc      60
ggtaggtatg gcaacgaata ttccacca                                        88

<210> SEQ ID NO 9
<211> LENGTH: 102
<212> TYPE: DNA
<213> ORGANISM: E. coli

<400> SEQUENCE: 9
tcgtacgctg ctgttgacct tcttctatcg tcagatgccg gaaattgttg aacgcggtca      60
cgtctacatc gctcagccgc cgctgtacaa agtgaagaaa gg                         102

<210> SEQ ID NO 10
<211> LENGTH: 96
<212> TYPE: DNA
<213> ORGANISM: Shigella boydii

<400> SEQUENCE: 10
actgtacctg gtggaagggg actccgcggg cggctctgcg aagcaggggc gcaaccgcaa      60
gaaccaggcg attctgccgc tgaagggtaa aatcct                                96

<210> SEQ ID NO 11
<211> LENGTH: 96
<212> TYPE: DNA
<213> ORGANISM: Shigella sonnei

<400> SEQUENCE: 11
actgtacctg gtggaagggg actccgcggg cggctctgcg aagcaagggc gtaaccgcaa      60
gaaccaggcg attctgccgc tgaagggtaa aatcct                                96

<210> SEQ ID NO 12
<211> LENGTH: 91
<212> TYPE: DNA
<213> ORGANISM: Shigella flexneri

<400> SEQUENCE: 12
aaccgcaaga accaggcgat tctgccgctg aagggtaaaa tccttaacgt cgagaaagcg      60
cgcttcgata agatgctctc ttctcaggaa g                                    91

<210> SEQ ID NO 13
<211> LENGTH: 17
<212> TYPE: DNA
<213> ORGANISM: Staphylococcus aureus

<400> SEQUENCE: 13
caccctcatg gtgactt                                                    17
```

-continued

```
<210> SEQ ID NO 14
<211> LENGTH: 18
<212> TYPE: DNA
<213> ORGANISM: Staphylococcus aureus

<400> SEQUENCE: 14
ataacgataa ctgaaatc                                                 18

<210> SEQ ID NO 15
<211> LENGTH: 19
<212> TYPE: DNA
<213> ORGANISM: Staphylococcus aureus

<400> SEQUENCE: 15
cgttgccata cctaccgct                                                19

<210> SEQ ID NO 16
<211> LENGTH: 17
<212> TYPE: DNA
<213> ORGANISM: Staphylococcus aureus

<400> SEQUENCE: 16
ccgctatacc tgatgct                                                  17

<210> SEQ ID NO 17
<211> LENGTH: 15
<212> TYPE: DNA
<213> ORGANISM: Staphylococcus aureus

<400> SEQUENCE: 17
ggtgactcat ctatc                                                    15

<210> SEQ ID NO 18
<211> LENGTH: 15
<212> TYPE: DNA
<213> ORGANISM: Staphylococcus aureus

<400> SEQUENCE: 18
attttagtca tacgt                                                    15

<210> SEQ ID NO 19
<211> LENGTH: 13
<212> TYPE: DNA
<213> ORGANISM: E. coli

<400> SEQUENCE: 19
gcgagttggg gca                                                      13

<210> SEQ ID NO 20
<211> LENGTH: 14
<212> TYPE: DNA
<213> ORGANISM: Shigella boydii

<400> SEQUENCE: 20
cgacggtact ttgc                                                     14

<210> SEQ ID NO 21
<211> LENGTH: 15
<212> TYPE: DNA
<213> ORGANISM: Shigella flexneri

<400> SEQUENCE: 21
ccgaaaacta cgctc                                                    15
```

```
<210> SEQ ID NO 22
<211> LENGTH: 16
<212> TYPE: DNA
<213> ORGANISM: E. coli

<400> SEQUENCE: 22
ccggaaattg ttgaac                                                       16

<210> SEQ ID NO 23
<211> LENGTH: 13
<212> TYPE: DNA
<213> ORGANISM: Shigella boydii

<400> SEQUENCE: 23
ggcgcaaccg caa                                                          13

<210> SEQ ID NO 24
<211> LENGTH: 13
<212> TYPE: DNA
<213> ORGANISM: Shigella sonnei

<400> SEQUENCE: 24
gcgaagcaag ggc                                                          13

<210> SEQ ID NO 25
<211> LENGTH: 16
<212> TYPE: DNA
<213> ORGANISM: Shigella flexneri

<400> SEQUENCE: 25
aaaatcctta acgtcg                                                       16

<210> SEQ ID NO 26
<211> LENGTH: 15
<212> TYPE: DNA
<213> ORGANISM: E. coli

<400> SEQUENCE: 26
actcggcagt ttatg                                                        15

<210> SEQ ID NO 27
<211> LENGTH: 91
<212> TYPE: DNA
<213> ORGANISM: E. coli
<220> FEATURE:
<221> NAME/KEY: misc_feature
<223> OTHER INFORMATION: GyrA gene

<400> SEQUENCE: 27
cgttggtgac gtaatcggta ataccatcc ccatggtgac tcggcggtct atgacacgat        60
cgtccgcatg gcgcagccat tctcgctgcg t                                      91

<210> SEQ ID NO 28
<211> LENGTH: 91
<212> TYPE: DNA
<213> ORGANISM: E. coli
<220> FEATURE:
<221> NAME/KEY: misc_feature
<223> OTHER INFORMATION: parC gene

<400> SEQUENCE: 28
accgaatccc ggttgtcgaa atattccgag ctgctattga gcgagctggg gcaggggacg        60
```

```
gctgactggg tgccaaactt cgacggcact t                                91
```

<210> SEQ ID NO 29
<211> LENGTH: 91
<212> TYPE: DNA
<213> ORGANISM: E. coli

<400> SEQUENCE: 29

```
cgagctgggg caggggacgg ctgactgggt gccaaacttc gacggcactt tgcaggagcc    60
gaaaatgcta cctgcccgtc tgccaaacat t                                   91
```

<210> SEQ ID NO 30
<211> LENGTH: 95
<212> TYPE: DNA
<213> ORGANISM: E. coli
<220> FEATURE:
<221> NAME/KEY: misc_feature
<223> OTHER INFORMATION: parC gene

<400> SEQUENCE: 30

```
tgcgtgaagt ggctcaggcg gcaatcgcat taatcgacca gccgaaaacc acgctcgatc    60
agctgctgga tatcgtgcag gggccggatt atccg                               95
```

<210> SEQ ID NO 31
<211> LENGTH: 98
<212> TYPE: DNA
<213> ORGANISM: E. coli
<220> FEATURE:
<221> NAME/KEY: misc_feature
<223> OTHER INFORMATION: GyrA gene

<400> SEQUENCE: 31

```
gtatcgttgg tgacgtaatg ggtaaatatc accctcatgg tgactcatct atttatgaag    60
caatggtacg tatggctcaa gatttcagtt atcgttat                            98
```

<210> SEQ ID NO 32
<211> LENGTH: 91
<212> TYPE: DNA
<213> ORGANISM: E. coli
<220> FEATURE:
<221> NAME/KEY: misc_feature
<223> OTHER INFORMATION: GyrA gene

<400> SEQUENCE: 32

```
ttcaatggat ggagatggcg cagcagcaat gcgttatact gaagcgcgta tgactaaaat    60
cacacttgaa ctgttacgtg atattaataa a                                   91
```

<210> SEQ ID NO 33
<211> LENGTH: 88
<212> TYPE: DNA
<213> ORGANISM: E. coli
<220> FEATURE:
<221> NAME/KEY: misc_feature
<223> OTHER INFORMATION: GyrB gene
<220> FEATURE:
<221> NAME/KEY: misc_feature
<223> OTHER INFORMATION: GyrA gene

<400> SEQUENCE: 33

```
gccgtcagtc ttacctgctc gattccctaa cttgttagcc aatggtgcat caggtatcgc    60
ggtaggtatg gcaacgaata ttccacca                                       88
```

<210> SEQ ID NO 34

-continued

```
<211> LENGTH: 102
<212> TYPE: DNA
<213> ORGANISM: E. coli
<220> FEATURE:
<221> NAME/KEY: misc_feature
<223> OTHER INFORMATION: GyrB gene

<400> SEQUENCE: 34
tcgtacgctg ctgttgacct tcttctatcg tcagatgccg gaaatcgttg aacgcggtca      60
cgtctacatc gctcagccgc cgctgtacaa agtgaagaaa gg                        102

<210> SEQ ID NO 35
<211> LENGTH: 96
<212> TYPE: DNA
<213> ORGANISM: E. coli
<220> FEATURE:
<221> NAME/KEY: misc_feature
<223> OTHER INFORMATION: GyrB gene

<400> SEQUENCE: 35
actgtacctg gtggaagggg actccgcggg cggctctgcg aagcaggggc gtaaccgcaa      60
gaaccaggcg attctgccgc tgaagggtaa aatcct                                96

<210> SEQ ID NO 36
<211> LENGTH: 91
<212> TYPE: DNA
<213> ORGANISM: E. coli
<220> FEATURE:
<221> NAME/KEY: misc_feature
<223> OTHER INFORMATION: GyrB gene

<400> SEQUENCE: 36
aaccgcaaga accaggcgat tctgccgctg aagggtaaaa tcctcaacgt cgagaaagcg      60
cgcttcgata agatgctctc ttctcaggaa g                                     91

<210> SEQ ID NO 37
<211> LENGTH: 102
<212> TYPE: DNA
<213> ORGANISM: E. coli
<220> FEATURE:
<221> NAME/KEY: misc_feature
<223> OTHER INFORMATION: GyrB gene

<400> SEQUENCE: 37
tcgtacgctg ctgttgacct tcttctatcg tcagatgccg gaattcgttg aacgcggtca      60
cgtctacatc gctcagccgc cgctgtacaa agtgaagaaa gg                        102
```